United States Patent
Hejazi

(10) Patent No.: US 11,206,864 B2
(45) Date of Patent: Dec. 28, 2021

(54) AEROSOL DELIVERY DEVICE PROVIDING FLAVOR CONTROL

(71) Applicant: RAI Strategic Holdings, Inc., Winston-Salem, NC (US)

(72) Inventor: Vahid Hejazi, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 715 days.

(21) Appl. No.: 15/935,105

(22) Filed: Mar. 26, 2018

(65) Prior Publication Data

US 2019/0289909 A1    Sep. 26, 2019

(51) Int. Cl.
*A24B 15/28* (2006.01)
*A24B 15/167* (2020.01)
(Continued)

(52) U.S. Cl.
CPC .......... *A24B 15/283* (2013.01); *A24B 15/167* (2016.11); *A24F 40/30* (2020.01); *A24F 40/42* (2020.01); *A24F 40/485* (2020.01); *A61M 11/041* (2013.01); *A61M 11/042* (2014.02); *A61M 15/0003* (2014.02); *A61M 15/0031* (2014.02); *A61M 15/06* (2013.01); *H05B 3/44* (2013.01); *A24F 40/10* (2020.01);
(Continued)

(58) Field of Classification Search
CPC ...... A24F 47/008; A24F 47/002; A24F 40/30; A24F 40/10; A24F 40/40; A24C 5/608; A24D 3/048; A61M 11/042; A61M 11/041; A61M 15/06; A61M 15/0003; A61M 15/0031; A24B 15/167; A24B 15/283

USPC .......................... 392/404; 239/302; 131/335
See application file for complete search history.

(56) References Cited

U.S. PATENT DOCUMENTS 2,057,353 A    10/1936   Whittemore, Jr.
2,104,266 A    1/1938    McCormick
(Continued)

FOREIGN PATENT DOCUMENTS

CN    1541577    11/2004
CN    2719043    8/2005
(Continued)

*Primary Examiner* — Tu B Hoang
*Assistant Examiner* — Alba T Rosario-Aponte
(74) *Attorney, Agent, or Firm* — Womble Bond Dickinson (US) LLP

(57) ABSTRACT

The present disclosure relates to a cartridge for use in an aerosol delivery device and an aerosol delivery device having the same. The cartridge includes a first reservoir configured to contain an aerosol precursor composition, and an atomizer having a liquid transport element in fluid communication with the first reservoir and a heating element configured to vaporize the aerosol precursor composition transported by the liquid transport element. The cartridge also includes a second reservoir, the second reservoir including two or more separate chambers, wherein at least one of the chambers contains a flavorant. A flow of air is configured to pass adjacent to the atomizer to entrain particles of the aerosol precursor composition that are vaporized by the heating element. The flow of air is also configured to pass at least one of the chambers of the second reservoir to entrain the flavorant of the respective chamber.

23 Claims, 8 Drawing Sheets

(51) Int. Cl.
*A61M 11/04* (2006.01)
*H05B 3/44* (2006.01)
*A61M 15/00* (2006.01)
*A61M 15/06* (2006.01)
*A24F 40/30* (2020.01)
*A24F 40/42* (2020.01)
*A24F 40/485* (2020.01)
*A61M 16/00* (2006.01)
*A24F 40/10* (2020.01)
*A24F 40/60* (2020.01)

(52) U.S. Cl.
CPC ............ *A24F 40/60* (2020.01); *A61M 15/002* (2014.02); *A61M 2016/0015* (2013.01); *A61M 2016/0024* (2013.01); *A61M 2016/0033* (2013.01); *A61M 2205/13* (2013.01); *A61M 2205/581* (2013.01); *A61M 2205/583* (2013.01); *A61M 2205/587* (2013.01); *A61M 2205/6018* (2013.01); *A61M 2205/6027* (2013.01); *A61M 2205/8206* (2013.01)

(56) References Cited

U.S. PATENT DOCUMENTS

| | | | |
|---|---|---|---|
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,261,424 | A | 11/1993 | Sprinkel, Jr. |
| 5,388,574 | A | 2/1995 | Ingebrethsen et al. |
| 5,530,225 | A | 6/1996 | Hajaligol |
| 5,687,746 | A | 11/1997 | Rose et al. |
| 5,726,421 | A | 3/1998 | Fleischhauer et al. |
| 5,865,185 | A | 2/1999 | Collins et al. |
| 5,894,841 | A | 4/1999 | Voges |
| 6,125,853 | A | 10/2000 | Susa et al. |
| 6,155,268 | A | 12/2000 | Takeuchi |
| 7,117,867 | B2 | 10/2006 | Cox et al. |
| 7,832,410 | B2 | 11/2010 | Hon |
| 8,314,591 | B2 | 11/2012 | Terry et al. |
| 8,365,742 | B2 | 2/2013 | Hon |
| 8,499,766 | B1 | 8/2013 | Newton |
| 10,021,912 | B2 * | 7/2018 | Yamada ................ A61M 15/06 |
| 2005/0016550 | A1 | 1/2005 | Katase |
| 2006/0196518 | A1 | 9/2006 | Hon |
| 2008/0092912 | A1 | 4/2008 | Robinson et al. |
| 2009/0095311 | A1 | 4/2009 | Hon |
| 2009/0126745 | A1 | 5/2009 | Hon |
| 2009/0188490 | A1 | 7/2009 | Hon |
| 2009/0272379 | A1 | 11/2009 | Thorens et al. |
| 2011/0094523 | A1 | 4/2011 | Thorens et al. |
| 2011/0126848 | A1 | 6/2011 | Zuber et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2011/0290248 | A1 | 12/2011 | Schennum |
| 2012/0111347 | A1 | 5/2012 | Hon |
| 2012/0260927 | A1 | 10/2012 | Liu |
| 2012/0279512 | A1 | 11/2012 | Hon |
| 2013/0037041 | A1 | 2/2013 | Worm et al. |
| 2013/0056013 | A1 | 3/2013 | Terry et al. |
| 2013/0306084 | A1 | 11/2013 | Flick |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0166029 | A1 | 6/2014 | Weigensberg et al. |
| 2014/0209105 | A1 | 7/2014 | Sears et al. |
| 2014/0251357 | A1 | 9/2014 | Tritz et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2016/0095356 | A1 * | 4/2016 | Chan ........................ H05B 3/44 131/329 |
| 2016/0143360 | A1 * | 5/2016 | Sanchez ................ A24F 47/008 239/302 |
| 2016/0262454 | A1 * | 9/2016 | Sears .................... A61M 11/042 |
| 2018/0184717 | A1 * | 7/2018 | Jiang ...................... A24F 40/44 |

FOREIGN PATENT DOCUMENTS

| | | | |
|---|---|---|---|
| CN | 201379072 | 1/2010 | |
| CN | 204070536 | 1/2015 | |
| EP | 0 295 122 | 12/1988 | |
| EP | 0 845 220 | 6/1998 | |
| EP | 1 618 803 | 1/2006 | |
| EP | 2989912 A1 * | 3/2016 | ........... A24F 47/008 |
| GB | 2469850 | 11/2010 | |
| WO | WO 2003/034847 | 5/2003 | |
| WO | WO 2004/080216 | 9/2004 | |
| WO | WO 2005/099494 | 10/2005 | |
| WO | WO 2007/131449 | 11/2007 | |
| WO | WO 2016/145072 | 9/2016 | |

* cited by examiner

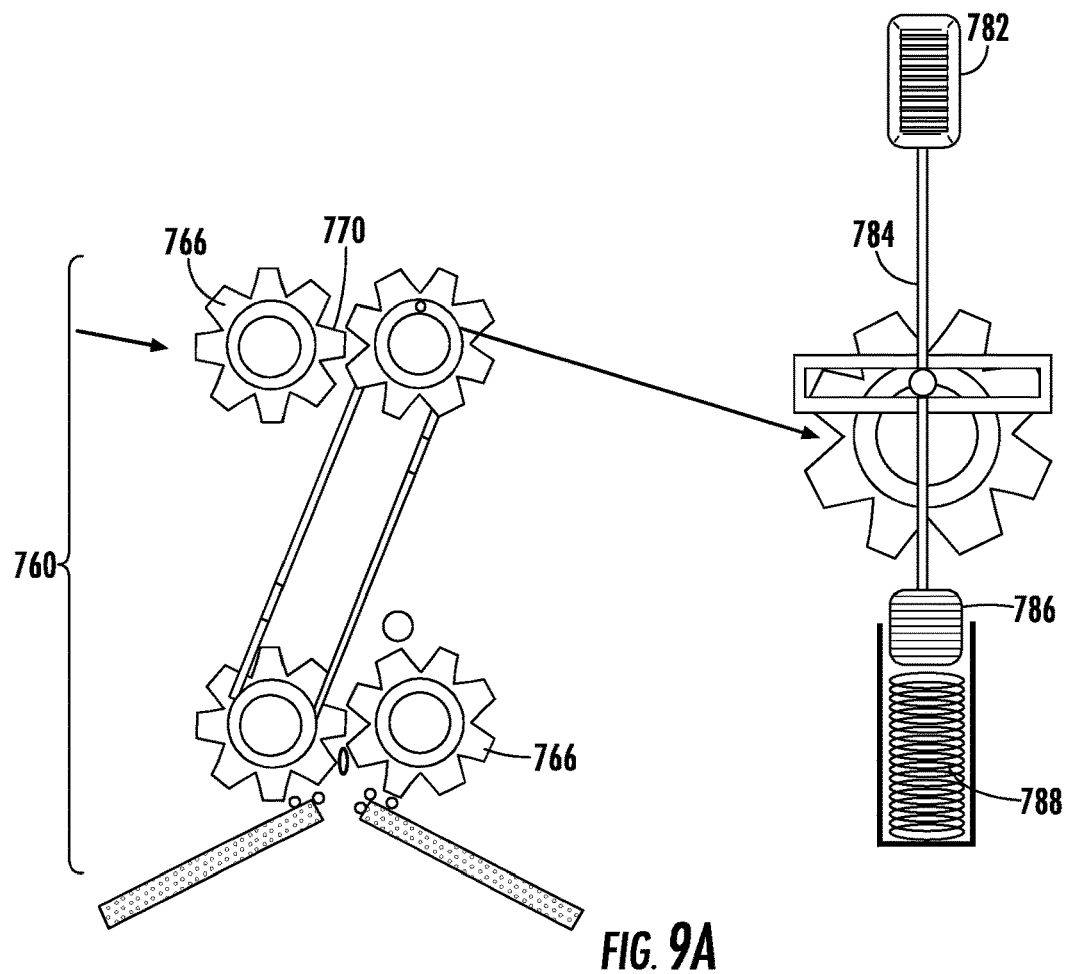
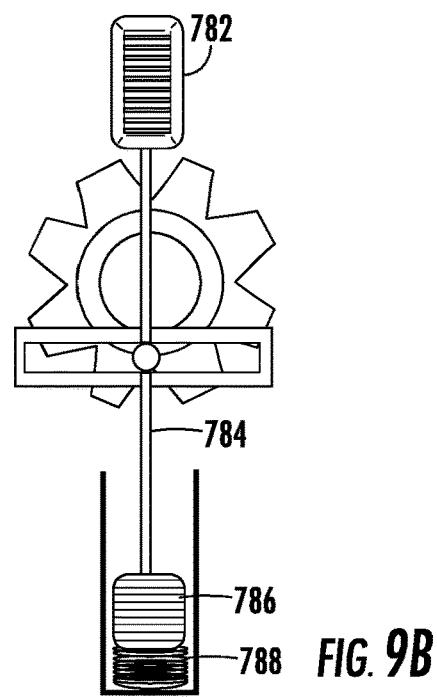
FIG. 9A
FIG. 9B

AEROSOL DELIVERY DEVICE PROVIDING FLAVOR CONTROL

FIELD OF THE DISCLOSURE

The present disclosure relates to aerosol delivery devices, and more particularly to an aerosol delivery device that include a reservoir and a vaporizing assembly, which may utilize electrical power to heat an aerosol precursor composition for the production of an aerosol. The aerosol precursor composition, which may incorporate materials and/or components that may be made or derived from tobacco or otherwise incorporate tobacco, is heated by the vaporizing assembly to produce an inhalable substance for human consumption.

BACKGROUND

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference.

The goal of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™, PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

Certain existing embodiments of aerosol delivery devices include a control body (i.e., a power source assembly) and a cartridge (i.e., a reservoir housing). A power source (e.g., a battery) may be positioned in the control body, and an aerosol precursor composition may be retained and/or stored within the cartridge. It would be desirable to provide a cartridge capable of adding one or more flavor additives to the aerosol precursor composition as desired by the user.

SUMMARY OF THE DISCLOSURE

In various implementations, the present disclosure provides a cartridge for use in an aerosol delivery device. In one implementation, the cartridge comprises a first reservoir configured to contain an aerosol precursor composition and an atomizer comprising a liquid transport element in fluid communication with the first reservoir and a heating element configured to vaporize the aerosol precursor composition transported by the liquid transport element. In the example implementation, the cartridge may further comprise a second reservoir, the second reservoir including two or more separate chambers, wherein at least one of the chambers contains a flavorant. The cartridge is configured to channel a flow of air to pass adjacent to the atomizer to entrain particles of the aerosol precursor composition that are vaporized by the heating element. The cartridge is configured to channel the flow of air to pass at least one of the chambers of the second reservoir to entrain the flavorant of the respective chamber.

In some implementations, the cartridge may further comprises at least one mask on one side of the second reservoir, the mask configured to permit the flow of air to pass therethrough, wherein the mask and the second reservoir are configured to be movable relative to one another such that the mask selectively and alternatively directs the flow of air passed a selected one or more of the chambers of the second reservoir.

In some implementations, the chamber of the second reservoir comprises an outer shell defining an inner surface that surrounds an inner passage formed by a porous tube, wherein the outer shell contains the flavorant, and wherein the inner passage is configured to allow the flow of air to pass through the chamber and entrain flavorant from the inner surface.

In some implementations, visual markings are provided the cartridge to designate the chambers of the second reservoir.

In some implementations, the chamber comprises a hopper for staging the flavorant. In one example, the chamber further comprises an actuator for selectively releasing flavorant from the hopper. In one implementation, the flavorant is encapsulated into a plurality of capsules. In one embodiment, the actuator is configured to break at least one of the capsules to release the flavorant. In one example implementation, the actuator comprises a pair of gears. The teeth of the gears can cooperate such that rotation of the gears is configured to release at least one capsule from the hopper, and release the flavorant from the capsule, wherein the flavorant is then entrained by the flow of air. In one example, the actuator is triggered by a mechanical button.

In some implementations, the cartridge further comprises a window into the hopper such that an amount of flavorant remaining in the hopper can be determined.

In various implementations, the present disclosure provides an aerosol delivery device. In one implementation, the aerosol delivery device comprises a control body and a cartridge. In various implementations, the cartridge comprises a first reservoir configured to contain an aerosol precursor composition, and an atomizer comprising a liquid transport element in fluid communication with the first reservoir and a heating element configured to vaporize the aerosol precursor composition transported by the liquid transport element. The cartridge of the example implementation may also include a second reservoir, the second reservoir including two or more separate chambers, wherein at least one of the chambers contains a flavorant. The cartridge is configured to channel a flow of air to pass adjacent to the atomizer to entrain particles of the aerosol precursor composition that are vaporized by the heating element. The cartridge is configured to channel the flow of air to pass at least one of the chambers of the second reservoir to entrain the flavorant of the respective chamber.

In some implementations, the cartridge further comprises at least one mask on one side of the second reservoir, the mask configured to the permit the flow of air to pass therethrough, wherein the mask and the second reservoir are configured to be movable relative to one another such that the mask selectively and alternatively directs the flow of air passed a selected one or more of the chambers of the second reservoir.

In some implementations of the aerosol delivery device, the chamber of the second reservoir of the cartridge comprises an outer shell defining an inner surface that surrounds an inner passage formed from a porous tube, wherein the outer shell contains the flavorant, and wherein the inner passage is configured to allow the flow of air to pass through the chamber and entrain flavorant from the inner surface.

In some implementations of the aerosol delivery device, visual markings are provided on at least one of the cartridge and the control body to designate the chambers of the second reservoir.

In some implementations of the aerosol delivery device, the chamber of the cartridge comprises a hopper for staging the flavorant. In some embodiments, the chamber further comprises an actuator for selectively releasing flavorant from the hopper. In some embodiments, the flavorant is encapsulated into a plurality of capsules. In some implementations, the actuator is configured to break at least one of the capsules to release the flavorant. In one implementation, the actuator comprises a pair of gears, wherein the teeth of the gears cooperate such that rotation of the gears is configured to release at least one capsule from the hopper and release the flavorant from the capsule, wherein the flavorant is then entrained by the flow of air. In one example, the actuator is triggered by a mechanical button.

In some implementations of the aerosol delivery device, the cartridge has a window into the hopper such that an amount of flavorant remaining in the chamber can be determined.

It will be appreciated that the above Summary is provided merely for purposes of summarizing some example aspects so as to provide a basic understanding of some aspects of the disclosure. As such, it will be appreciated that the above described example aspects are merely examples of some aspects and should not be construed to narrow the scope or spirit of the disclosure in any way. It will be appreciated that the scope of the disclosure encompasses many potential aspects, some of which will be further described below, in addition to those here summarized. Further, other features, aspects, and advantages of the disclosure will be apparent from a reading of the following detailed description taken in conjunction with the accompanying drawings which illustrate, by way of example, the principles of the described aspects.

BRIEF DESCRIPTION OF THE FIGURES

In order to assist the understanding of aspects of the disclosure, reference will now be made to the appended drawings, which are not necessarily drawn to scale and in which like reference numerals refer to like elements. The drawings are exemplary only, and should not be construed as limiting the disclosure.

FIGS. 9A and 9B illustrate one example implementation for actuating the flavor adding module of FIG. 8.

DETAILED DESCRIPTION

Figure 1:
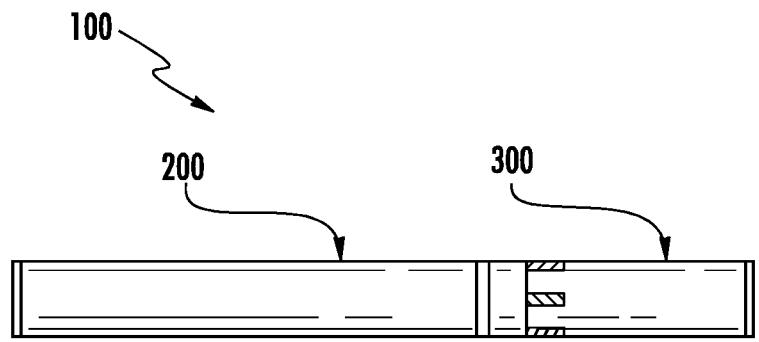
FIG. 1 illustrates a side view of an aerosol delivery device comprising a cartridge and a control body in an assembled configuration, according to an example implementation of the present disclosure.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of aerosol delivery devices. The aerosol delivery devices may use electrical energy to heat a material to form an inhalable substance; such articles may be sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device, although in other implementations the aerosol may not be visible. In some implementations, aerosol delivery devices may incorporate tobacco and/or components derived from tobacco. As such, the aerosol delivery device can be characterized as an electronic smoking article such as an electronic cigarette or "e-cigarette."

While the systems are generally described herein in terms of implementations associated with aerosol delivery devices such as so-called "e-cigarettes," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one implementation, all of the components of the aerosol delivery device are contained within one outer body or shell. Alternatively, an aerosol delivery device can comprise two or more shells that are joined and are separable. For example, an aerosol delivery device can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure may comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance or inductive heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (which may itself contain one or more flavorants, medicaments, or other additives) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery and/or other electrical power source (e.g., a capacitor) to provide current flow sufficient to provide various functionalities to the aerosol delivery device, such as powering of a heater, powering of control systems, powering of indicators, and the like. The power source can take on various implementations. In one example, the power source is able to deliver sufficient power to rapidly heat the heating element to provide for aerosol formation and power the aerosol delivery device through use for a desired duration of time. The power source may be sized to fit conveniently within the aerosol delivery device so that the aerosol delivery device can be easily handled. Additionally, in one embodiment, a power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

One example implementation of an aerosol delivery device 100 is illustrated in FIG. 1. In particular, FIG. 1 illustrates an aerosol delivery device 100 including a control body 200 and a cartridge 300. The control body 200 and the cartridge 300 can be permanently or detachably aligned in a functioning relationship. Various mechanisms may connect the cartridge 300 to the control body 200 to result in a threaded engagement, a press-fit engagement, an interference fit, a magnetic engagement, or the like. The aerosol delivery device 100 may be substantially rod-like, substantially tubular shaped, or substantially cylindrically shaped in some implementations when the cartridge 300 and the control body 200 are in an assembled configuration. However, as noted above, various other configurations such as rectangular or fob-shaped may be employed in other implementations. Further, although the aerosol delivery devices are generally described herein as resembling the size and shape of a traditional smoking article, in other implementations differing configurations and larger capacity reservoirs, which may be referred to as "tanks," may be employed.

In specific implementations, one or both of the cartridge 300 and the control body 200 may be referred to as being disposable or as being reusable. For example, the control body 200 may have a replaceable battery or a rechargeable battery and/or capacitor and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations the cartridge 300 may comprise a single-use cartridge, as disclosed in U.S. Pat. No. 8,910,639 to Chang et al., which is incorporated herein by reference in its entirety. For example, the cartridge 300 may include a limited amount of aerosol precursor composition therein to provide for many of the sensations (e.g., inhalation and exhalation rituals, types of tastes or flavors, organoleptic effects, etc.) of smoking a particular amount of traditional types of smoking articles (e.g., cigarettes, cigars, pipes, etc.). In some aspects, the cartridge 300 may include a particular amount of aerosol precursor composition therein equivalent to the amount of traditional types of smoking articles one would consume to obtain the sensations of smoking a typical amount of traditional types of smoking articles (e.g., a typical package of cigarettes—i.e., twenty (20) cigarettes).

Figure 2:
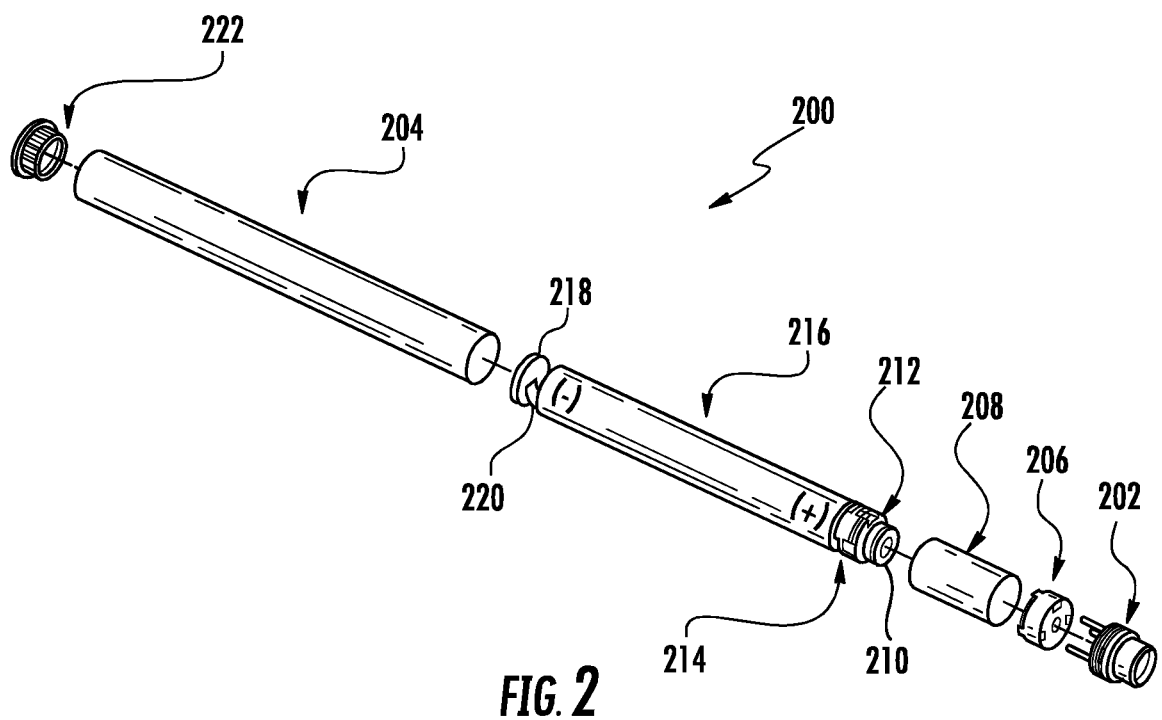
FIG. 2 illustrates an exploded perspective view of the control body of FIG. 1, according to an example implementation of the present disclosure.

FIG. 2 illustrates an exploded view of the control body 200 of the aerosol delivery device 100 (see, FIG. 1) according to an example implementation of the present disclosure. As illustrated, the control body 200 may comprise a coupler 202, an outer body 204, a sealing member 206, an adhesive member 208 (e.g., KAPTON® tape), a flow sensor 210 (e.g., a puff sensor or pressure switch), a control component 212, a spacer 214, an electrical power source 216 (e.g., a capacitor and/or a battery, which may be rechargeable), a circuit board with at least one indicator 218, such as a light emitting diode (LED) that can communicate with the consumer the condition of the battery, flavor, liquid, and/or their combination, using different types of sensors (pressure, resistance, humidity, etc.), a connector circuit 220, and an end cap 222. Examples of electrical power sources are described in U.S. Pat. No. 9,484,155 to Peckerar et al., the disclosure of which is incorporated herein by reference in its entirety.

With respect to the flow sensor 210, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In one implementation the indicator 218 may comprise one or more light emitting diodes. The indicator 218 can be in communication with the control component 212 through the connector circuit 220 and be illuminated, for example, during a user draw on a cartridge coupled to the coupler 202, as detected by the flow sensor 210. The end cap 222 may be adapted to make visible the illumination provided thereunder by the indicator 218. Accordingly, the indicator 218 may be illuminated during use of the aerosol delivery device 100 to simulate the lit end of a smoking article. However, in other implementations the indicator 218 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

Figure 3:
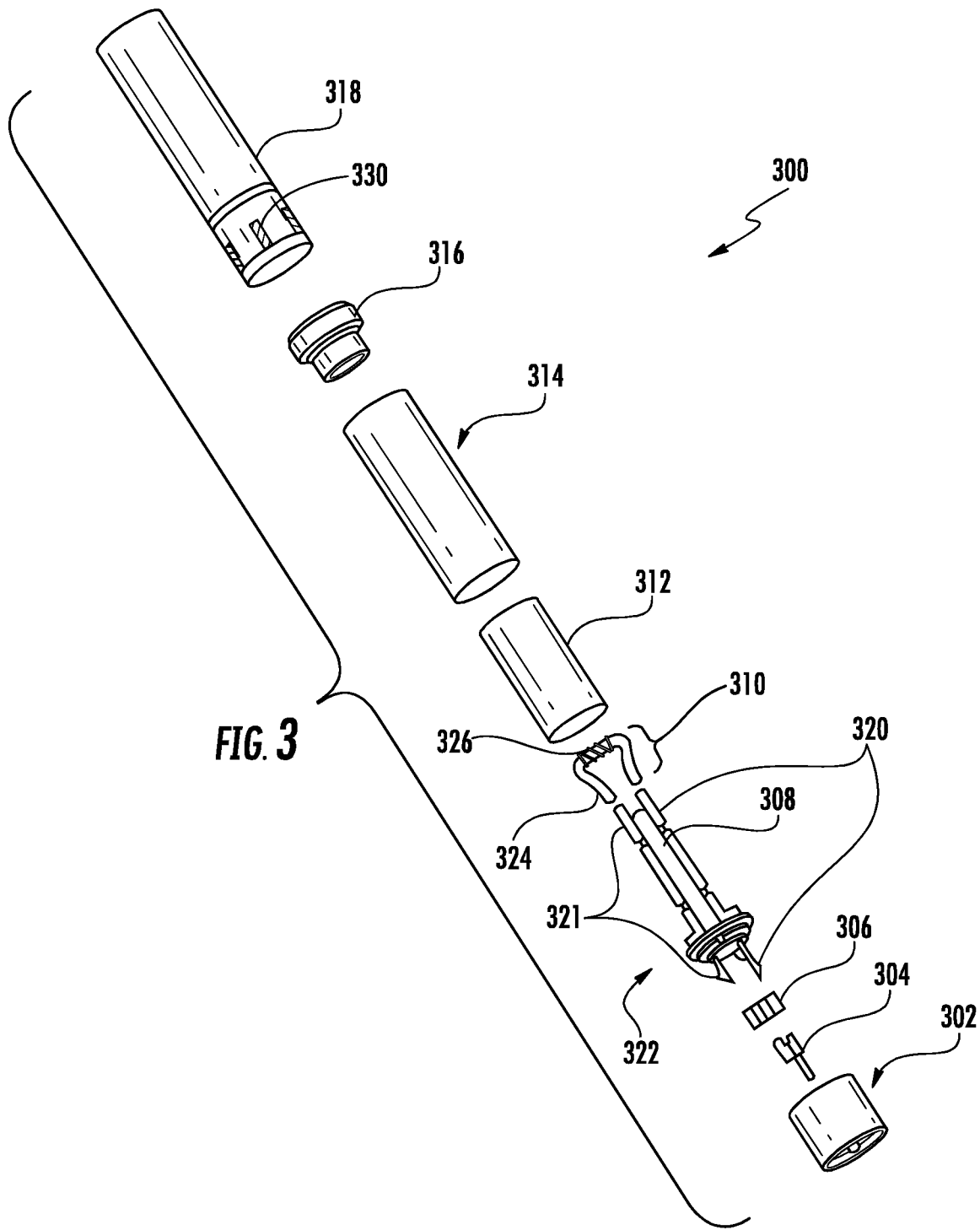
FIG. 3 illustrates an exploded perspective view of the cartridge of FIG. 1, according to an example implementation of the present disclosure.

FIG. 3 illustrates the cartridge 300 of the aerosol delivery device 100 (see, FIG. 1) in an exploded configuration. As illustrated, the cartridge 300 may comprise a base 302, a control component terminal 304, an electronic component 306, a flow director 308, an atomizer 310, a reservoir 312 (e.g., a liquid tank or a reservoir substrate), an outer body 314, a mouthpiece 316, a label 318, and first and second heating terminals 320, 321 according to an example embodiment of the present disclosure. Markings 330 may be applied to the label 318 or the outer body 314 to provide the user with indicators of internal components or functionality such as flavor reservoirs as discussed below.

In some implementations the first and second heating terminals 320, 321 may be embedded in, or otherwise coupled to, the flow director 308. For example, the first and second heating terminals 320, 321 may be insert molded in the flow director 308. Accordingly, the flow director 308 and the first and second heating terminals are collectively referred to herein as a flow director assembly 322. Additional description with respect to the first and second heating terminals 320, 321 and the flow director 308 is provided in U.S. Pat. Pub. No. 2015/0335071 to Brinkley et al., which is incorporated herein by reference in its entirety.

The atomizer 310 of the depicted implementation may comprise a liquid transport element 324 and a heating element 326. The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. Pat. No. 9,220,302 to Depiano et al., which is incorporated herein by reference in its entirety.

The base 302 may be coupled to a first end of the outer body 314 and the mouthpiece 316 may be coupled to an opposing second end of the outer body to substantially or fully enclose other components of the cartridge 300 therein. For example, the control component terminal 304, the electronic component 306, the flow director 308, the atomizer 310, and the reservoir 312 may be substantially or entirely retained within the outer body 314. The label 318 may at least partially surround the outer body 314, and optionally the base 302, and include information such as a product identifier thereon. The base 302 may be configured to engage the coupler 202 of the control body 200 (see, e.g., FIG. 2). In some implementations the base 302 may comprise anti-rotation features that substantially prevent relative rotation between the cartridge and the control body as disclosed in U.S. Pat. App. Pub. No. 2014/0261495 to Novak et al., which is incorporated herein by reference in its entirety.

The reservoir 312 may be configured to hold an aerosol precursor composition. Some representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference in their entireties.

The reservoir 312 may comprise a plurality of layers of nonwoven fibers formed into the shape of a tube encircling the interior of the outer body 314 of the cartridge 300. Thus, liquid components, for example, can be sorptively retained by the reservoir 312. The reservoir 312 is in fluid connection with the liquid transport element 324. Thus, the liquid transport element 324 may be configured to transport liquid from the reservoir 312 to the heating element 326 via capillary action or other liquid transport mechanism. The reservoir 312 is not limited to the absorptive reservoir substrate type. The reservoir 312 may comprises a housing or tank that retains aerosol precursor in free flowing liquid form. The reservoir 312 may or may not be re-fillable.

As illustrated, the liquid transport element 324 may be in direct contact with the heating element 326. As further illustrated in FIG. 3, the heating element 326 may comprise a wire defining a plurality of coils wound about the liquid transport element 324. In some embodiments the heating element 326 may be formed by winding the wire about the liquid transport element 324 as described in U.S. Pat. No. 9,210,738 to Ward et al., which is incorporated herein by reference in its entirety. Further, in some implementations the wire may define a variable coil spacing, as described in U.S. Pat. No. 9,277,770 to DePiano et al., which is incorporated herein by reference in its entirety. Various implementations of materials configured to produce heat when electrical current is applied therethrough may be employed to form the heating element 326. Example materials from which the wire coil may be formed include Kanthal (Fe-CrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic).

However, various other implementations of methods may be employed to form the heating element 326, and various other implementations of heating elements may be employed in the atomizer 310. For example, a stamped heating element may be employed in the atomizer, as described in U.S. Pat. App. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other implementations. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various implementations, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

The first heating terminal 320 and the second heating terminal 321 (e.g., negative and positive heating terminals) are configured to engage opposing ends of the heating element 326 and to form an electrical connection with the control body 200 (see, e.g., FIG. 2) when the cartridge 300 is connected thereto. Further, when the control body 200 is coupled to the cartridge 300, the electronic component 306 may form an electrical connection with the control body through the control component terminal 304. The control body 200 may thus employ the electronic control component 212 (see, FIG. 2) to determine whether the cartridge 300 is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on the mouthpiece 316 of the cartridge 300 of the aerosol delivery device 100 (see, FIG. 1). This may pull air through an opening in the control body 200 (see, e.g., FIG. 2) or in the cartridge 300. For example, in one implementation an opening may be defined between the coupler 202 and the outer body 204 of the control body 200 (see, e.g., FIG. 2), as described in U.S. Pat. No. 9,220,302 to DePiano et al., which is incorporated herein by reference in its entirety. However, the flow of air may be received through other parts of the aerosol delivery device 100 in other implementations. As noted above, in some implementations the cartridge 300 may include the flow director 308. The flow director 308 may be configured to direct the flow of air received from the control body 200 to the heating element 326 of the atomizer 310.

A sensor in the aerosol delivery device 100 (e.g., the flow sensor 210 in the control body 200; see, FIG. 2) may sense the puff. When the puff is sensed, the control body 200 may direct current to the heating element 326 through a circuit including the first heating terminal 320 and the second heating terminal 321. Accordingly, the heating element 326 may vaporize the aerosol precursor composition directed to an aerosolization zone from the reservoir 312 by the liquid transport element 324. Thus, the mouthpiece 326 may allow passage of air and entrained vapor (i.e., the components of the aerosol precursor composition in an inhalable form) from the cartridge 300 to a consumer drawing thereon.

Various other details with respect to the components that may be included in the cartridge 300 are provided, for example, in U.S. Pat. App. Pub. No. 2014/0261495 to DePiano et al., which is incorporated herein by reference in its entirety. Additional components that may be included in the cartridge 300 and details relating thereto are provided, for example, in U.S. Pat. Pub. No. 2015/0335071 to Brinkley et al., filed May 23, 2014, which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In another implementation, substantially the entirety of the cartridge may be formed from one or more carbon materials, which may provide advantages in terms of biodegradability and absence of wires. In this regard, the heating element may comprise carbon foam, the reservoir may comprise carbonized fabric, and graphite may be employed to form an electrical connection with the power source and control component. An example embodiment of a carbon-based cartridge is provided in U.S. Pat. App. Pub. No. 2013/0255702 to Griffith et al., which is incorporated herein by reference in its entirety.

However, in some implementations it may be desirable to provide aerosol delivery devices, and in particular, cartridges for use in aerosol delivery devices, with alternative configurations. In this regard, FIG. 4 illustrates a schematic cross sectional view of a cartridge 500 for use in an aerosol delivery device, according to a first example implementation of the present disclosure. Where not otherwise described and/or illustrated, components of an aerosol delivery device, and in particular, the control body for use with the illustrated cartridge, may be substantially similar to, or the same as, corresponding components described above.

As illustrated in FIGS. 4-6, and as will be discussed in more detail below, the cartridge 500 of the depicted implementation includes the following components: a mouth piece 504, a primary reservoir 508, an atomizer 510 (which includes a liquid transport element 512 and a heating element 514), a flavor adding assembly 520, which includes a flavor reservoir 522, and a flavor selector in the form of a mask 524 that provides for an air flow path controller, and a cartridge base 530 configured to provide a mechanical and electrical connection between the cartridge and the control body. As understood from the discussion above, the cartridge 500 of FIGS. 4-6 may be configured to releasably engage a control body with the cartridge base 530 so as to create an aerosol delivery device. In various implementations, the control body may be similar to, or the same as, the control body 200 described above (see, FIG. 2), and hence description thereof will not be repeated. It should be noted, however, that in other implementations the control body may differ from that described above. In addition, in some implementations, the control body of the aerosol delivery device may have a different shape than that described above, such as, for example, a hand-held fob-shaped control body.

In various implementations, the primary reservoir 508 may be a tank type reservoir constructed of one or more of a variety of materials, including, for example, a metal material, a glass material, a ceramic material, and/or a plastic material, such as, for example, an acrylic material (e.g., polymethlamethacrylate, polyethylene, polyester, etc.). In some implementations, the primary reservoir 508 may comprise a translucent or transparent material, such that a user may view the quantity of the aerosol precursor composition remaining therein. In one implementation, the primary reservoir 508 is constructed of polycarbonate or polypropelene or Tritan™. In some embodiments, the primary reservoir 508 is in the form of a tank for containing liquid aerosol precursor composition in a free flowing manner. In alternative embodiments, the primary reservoir 508 may include a porous material for retaining the aerosol precursor composition as discussed above with respect to the reservoir 312 (FIG. 3).

The cartridge base 530 of the cartridge 500 and the corresponding connector of the control body 200 (FIG. 2) are configured such that, when attached together, the cartridge base and the control body do not easily move relative to each other. It should be noted that such a relationship may be created using any suitable connecting means as discussed above. For example, in some implementations, the cartridge base and the control body may be connected using a threaded connection, a magnet connection, a snap connection, and/or a bayonet connection, wherein the cartridge base (or the control body) may include one or more pins, and the control body (or cartridge base) may include one or more corresponding L-shaped slots.

As discussed above, one aspect of the cartridge base 530 may be to provide an electrical connection with the power source 216 of the control body 200 (FIG. 2) such that electrical current can be selectively supplied to the atomizer 510, and more particularly, the heating element 514.

In various implementations, the liquid transport element 512 may comprise a porous monolith. For example, in the depicted implementation, the liquid transport element 512 may comprise a ceramic material such that aerosol precursor composition delivered to the liquid transport element 512 may be absorbed therein for aerosolization. In another example, the transport element 512 may be formed from silica fiber, cotton, mesh, other porous metals, or other cellulose based materials. In one embodiment, a ceramic liquid transport element with a precise shape can be manufactured using additive manufacturing or 3D printing techniques. The liquid transport element 512 can be fixed directly into holes created on the primary reservoir 508.

Alternatively, an additional spongy disk, such as a porous pad made of highly absorptive polymers, ceramics, etc., can interface between the liquid transport element 512 and the primary reservoir 508. In various implementations, the heating element 514 may be wrapped or coiled around the liquid transport element 512, as shown. In some implementations, the wire of the heating element 514 may comprise titanium, Kanthal (FeCrAl), Nichrome, nickel, stainless steel, Molybdenum disilicide ($MoSi_2$), molybdenum silicide (MoSi), Molybdenum disilicide doped with Aluminum ($Mo(Si,Al)_2$), graphite and graphite-based materials; ceramic (e.g., a positive or negative temperature coefficient ceramic), Tungsten, and Tungsten-based alloys, or any other suitable materials, such as those noted elsewhere herein. Tungsten and Tungsten-based alloys may be useful in that these materials may define a coefficient of expansion suitable for usage with many ceramics, which may be employed in the liquid transport element 512.

As noted, according to some implementations, the atomizer 510 may be formed by winding a wire about a liquid transport element as described in U.S. Pat. No. 9,210,738 to Ward et al., which is incorporated herein by reference in its entirety. However, various other methods may be employed to form the atomizer 510, and various other implementations of a heating element may be employed in the atomizer. For example, a metal mesh could be positioned around a cylindrical wick, or a ribbon-like metal mesh could be positioned on a ribbon-shaped or sheet-shaped wick. For example, a heating element may be configured to heat the aerosol precursor composition disposed within a liquid transport element via radiant heating, as described in U.S. Pat. App. Pub. No. 2017/0020193, filed Dec. 3, 2015, the content of which is incorporated herein by reference in its entirety. In another implementation, the heating element 514 may be configured to heat the aerosol precursor composition via inductive heating, as described in U.S. Pat. App. Pub. No. 2017/0127722, filed Nov. 6, 2015, the content of which is incorporated herein by reference in its entirety. A variety of heater components may be used in the present aerosol delivery device. In various implementations, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

Although not depicted in this manner, in some implementations, the wire of the heating element 514 may be at least partially imbedded in the liquid transport element 512. In this regard, in the case of a ceramic liquid transport element 512, the wire of the heating element 514 may be imbedded in the liquid transport element 512 before the liquid transport element 512 is fired in a high temperature oven known as a kiln. For example, the wire may be wrapped about a long section of the base material from which the ceramic is formed prior to firing the material. Examples of such base materials employed to form the ceramic in the liquid transport element 512 may include clay, oxides, nonoxides, and composites. Thereby, the wire may at least partially imbed in the base material during wrapping thereabout. The base material and the wire may then be fired in the kiln. Afterwards, a saw or other cutting device may divide the product into individual atomizers having a desired length. In another embodiment, the heating element can be placed at least partially into the wick after ceramic firing, with the heating element in channels in the ceramic formed using additive manufacturing or a 3D printing technique.

In the depicted implementation, an atomizer chamber 540 is formed around the atomizer 510. The atomizer chamber 540 is in fluid communication with an aerosol channel 546 that passes through the primary reservoir 508 and terminates at an opening 548 through the mouth piece 504 of the cartridge 500.

Figure 5:
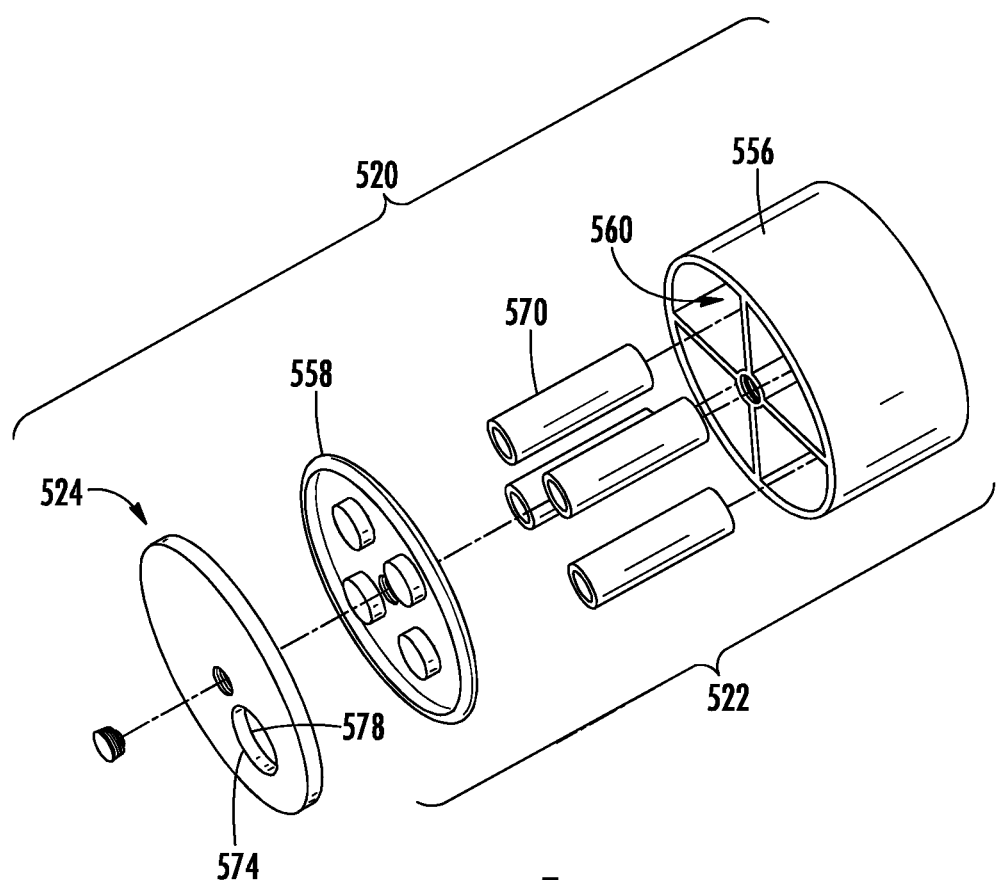
FIG. 5 illustrates an exploded view of a flavor adding assembly according to an example implementation of the cartridge of FIG. 4.

FIG. 5 illustrates greater detail of the flavor adding assembly 520 through an exploded perspective view. In the illustrated embodiment, the flavor adding assembly 520 is positioned upstream of the atomizer chamber 540. In other embodiments, the flavor adding assembly 520 may be positioned downstream of the atomizer chamber 540. The flavor adding assembly 520 includes the flavor reservoir 522 and the mask 524. The flavor reservoir 522 may include a housing 556 and a lid 558. The housing 556 and the lid 558 may be composed of polymers (acetate, PE, PP, silicone, polyester, polyurethane, etc.), or ceramics (e.g., alumina), or metals (e.g., aluminum). The housing 556 may be provided in the form of a tray that is configured to be removable from the cartridge 500. The flavor reservoir 522 and the mask 524 may form a module that can be easily assembled as part of the cartridge 500, or may alternatively provide an interchangeable portion of the cartridge.

In the illustrated embodiment, the flavor reservoir 522 is divided into four separate chambers or flavor sections 560. The present disclosure is not limited to four flavor sections 560, but may have a lesser or greater number of flavor sections. Each of the flavor sections 560 is configured to stage a flavorant that can be selectively added to the aerosol that exits the opening 548 in the mouth piece 504. Each flavor section 560 may contain a flavorant, though one the flavor sections 560 of the flavor reservoir 522 may be intentionally left empty to allow the user to receive aerosol containing only the aerosol precursor composition within the primary reservoir 508. An empty flavor section 560 may be referred to as a bypass section of the flavor reservoir 522.

Each flavor section 560 may constitute its own reservoir. In one example, the user would be able to build their own unique combination of flavor sections 560, including the possibility of selecting each flavor section to contain the same flavorant.

In some implementations, a flavor section 560 may comprise a section of the flavor reservoir 522 that includes a flavorant. The flavorant may be provided as a liquid, solid, or gel, which may be in the form of separate beads or particles. In other implementations, a flavor section 560 may comprise a substrate or other material in which the flavorant is absorbed or otherwise contained. For example, in some implementations, a flavor section 560 may comprise carbon materials, ceramics, polymers, composites, metals, cellulosics, and the like.

Figure 6:
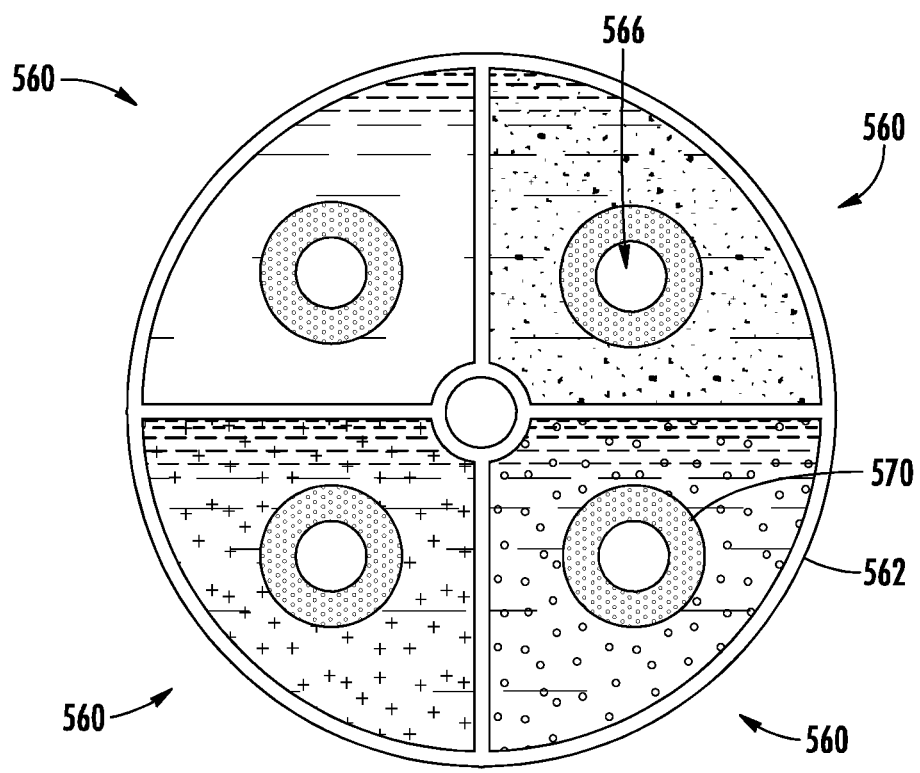
FIG. 6 illustrates a schematic view of a flavor reservoir according to an example implementation of the flavor adding assembly of FIG. 5.

As shown in FIG. 6, a flavor section 560 may include an outer shell 562, formed by the housing 556, and defining an inner surface that surrounds an inner passage 566. The outer shell 562 is configured to contain the flavorant. The inner passage 566 is configured to allow a draw of air to pass through the flavor section 560 and entrain flavorant from the inner surface. The inner surface may be defined by a wick 570, particularly a tubular shaped wick, which provides the interface between the inner passage 566 and the contents of the outer shell 562. The wick 570 may be a nanoporous, microporous and/or macroporous tube made from polymers (such as polyethylene or polyester fibers, etc.) or ceramics (such as alumina, silica, zirconia, etc.) that absorbs flavorant, such as liquid flavorant, from within the outer shell 562, and transports the liquid flavorant through capillary action into fluid contact with the inner passage 566, where particles of the flavorant can be entrained by a draw of air passing through the inner passage. The material of the wick 570 is not particularly limited, and may include any of the materials suitable for the fluid transfer element 324 (FIG. 3) as discussed above.

In various implementations, the aerosol precursor composition held within the primary reservoir 508 may comprise an unflavored aerosol precursor composition, though a flavored aerosol precursor composition (i.e., an aerosol precursor composition that includes one or more flavorants) is also contemplated. The flavor sections 560 then include one or more flavorants, which may themselves be provided in the form of compositions with aerosol precursor components. As used herein, reference to a "flavorant" refers to compounds or components that can be aerosolized and delivered to a user and which impart a sensory experience in terms of taste and/or aroma. Exemplary flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Exemplary plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Figure 4:
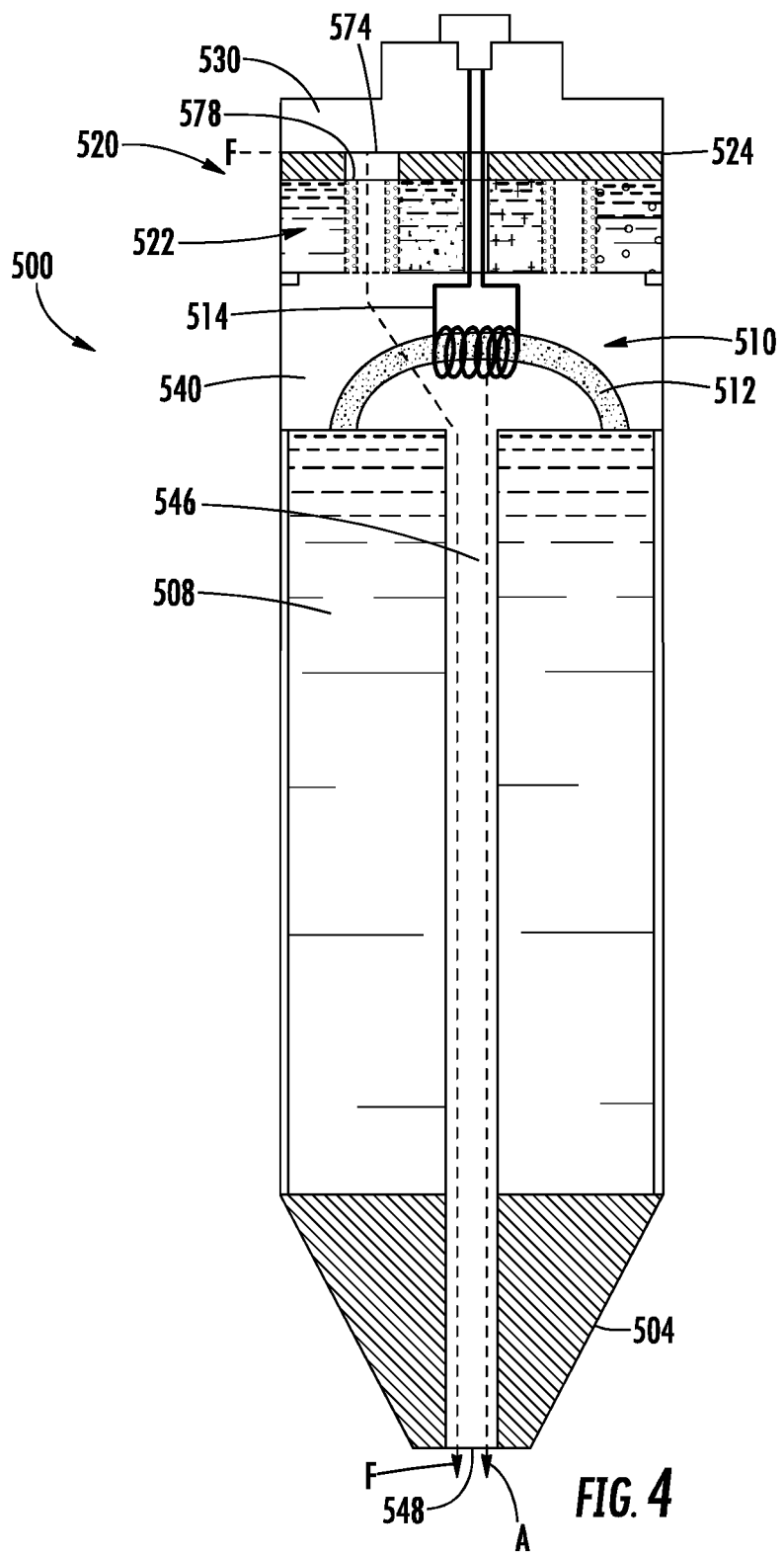
FIG. 4 illustrates a schematic cross section of a cartridge for use in an aerosol delivery device according to an example implementation of the present disclosure.

Returning to FIG. 5, the mask 524 may be formed from polymers, ceramics, or metals. The mask 524 acts as an air flow controller to direct the flow of air, which may be associated with a draw by the user on the mouth piece 504 (FIG. 4), selectively through the inner passage 566 of one or more of the flavor sections 560 such that flavorant is entrained by the flow of air prior to arriving in the atomizer chamber 540 (FIG. 4). In one implementation, the flow of air begins at an opening in the cartridge 300 between the base 530 and the mask 524 to arrive at an inlet 574 of the mask. In another implementation, the path of the flow of air may begin at an opening in the coupler 202 of the control body 200 (FIG. 2). The flow of air may then exit the mask 524 through an outlet 578 (FIG. 4). In the illustrated example, the inlet 574 and the outlet are directly opposite one another on the opposite faces of the disk-shaped mask 524. In another embodiment, not shown, the inlet may be centrally located within a first side of the disk-shaped mask. The outlet may be located on a second, opposite side of the mask at a location offset from the center. One skilled in the art will appreciate that the resulting mask 524 may be substantially hollow or otherwise provide a passage from the inlet 574 to the outlet. The arrangement of the inlet 574 and the outlet of the mask 524 are not particularly limited so long as at least one inlet 574 is able to receive the flow of air regardless of the position of the mask 524 relative to the fluid reservoir 522. Further, the arrangement of the outlet is configured to selectively direct the flow of air through or passed the desired one or more of the flavor sections 560.

In another implementation, the mask 524 may be located downstream of the flavor reservoir 522. In this implementation, instead of directly flow into a desired flavor section 560, the mask may act to only permit the flow of air to exit from the desired flavor section.

In another embodiment, not shown, a second mask can be installed between the flavor reservoir 522 and the atomizer chamber 540. The second mask may rotate with the mask 525 in order to help prevent unintentional release of flavor particles from the flavor sections 560 into the atomizer chamber 540.

In another example, not illustrated, the mask 524 may be a ring-shape that surrounds the cartridge 500. The flow of air may begin at the inlet 574 of the mask 524, and the outlet 578 of the mask 524 may be selectively arranged with respect to a plurality of openings into the cartridge body, wherein each opening facilitates passage of the flow of air to and through an inner passage 566 of a select one of the flavor sections 560.

In various implementations, the mask 524 may be configured to be rotatably attached relative to the flavor reservoir 522. In operation (referring to FIG. 4), the cartridge 500 is removably attached to the control body 200 via the cartridge base 530. The mask 524 is assembled with the cartridge 500 to be adjustable, for example rotatable, relative to the flavor reservoir 522 to selectively direct a flow of air F through a desired flavor section 560 or bypass section of the flavor reservoir. Thus, a consumer may selectively align the outlet 578 of the mask 524 with a selected flavor section 560 by adjusting the mask to the appropriate location relative to the flavor reservoir 522. In one example, the flavor reservoir 522 is fixed in the cartridge 500. Then, the mask 524 can be either fixed relative to the control body 200 or is able to rotate relative to the control body 200. Therefore the mask 524 may rotate independently or selection of the flavor section 560 can occur by rotating the control body 200 relative to the cartridge 500.

In various implementations, the cartridge 500 and/or control body may include one or more indicators to aid the consumer in determining a rotation location. For example, in some implementations the cartridge 500 and/or the control body may include visual indicators, such as a plurality of markings 330 (FIG. 3), thereon so as to indicate the locations of the various flavor sections of the flavor reservoir 522. Alternatively, or in addition, the cartridge 500 and/or control body may include one or more audible or tangible indicators, such as, for example, a series of detents (which, in some implementations, may also include a sound) that indicate the location of the various flavor sections. The detents, for example, may be provided to ensure proper alignment between the outlet 578 of the mask 524 and the flavor section 560. In the instance that there are four flavor sections 560, the markings 330 and detents may be spaced equally 90 degrees apart around the circumference of the cartridge 300 to provide for a predetermined degree of rotation per flavor section. It should be noted that in some implementations, one or more of any of the components described above may be able to move relative to the others without affecting the operation of the device.

An electrical connection between the control body 200 (FIG. 1) and the atomizer 510 (FIG. 5) via the two ends of the heating element 514, for example including an electrically connector provided through the mask 524, allows the control body 200 to direct electrical current to the atomizer 510, such as upon actuation by the user (e.g., via a button) and/or when a puff on the aerosol delivery device is detected. A puff may be detected by a change in the electrical resistance of a material that can be folded or bent by the air flow F drawn by the consumer. When a user draws on the mouth piece 504 of the cartridge 500, a flow of air F (see FIG. 4) may be directed through one or more air intakes in the cartridge base 530 from the environment. The flow of air F drawn through the air intake(s) may then be drawn through one or more inner passages 566 of one or more flavor sections 560 of the flavor reservoir 522 as facilitated by the mask 524.

Simultaneously, a flow sensor (see e.g., FIG. 2) may detect the draw. Thereby, the control body 200 may direct current through the heating element 514 to heat the atomizer 510. As the atomizer 510 heats, the aerosol precursor composition from the primary reservoir 508 may be vaporized at the atomizer 510 directly or via heating of the liquid transport element 512. Accordingly, the resultant vapor or aerosol A may be produced within the atomizer chamber 540, mixed with entrained flavorant picked up by the flow of air F passing though the inner passage 566 of the selected flavor section 560 and then travel through the aerosol channel 546, and out of the opening 548 of the mouth piece 504 to the user.

The use of the cartridge 500 in association with a control body 200 (FIG. 2) may be characterized by a method of forming aerosol for consumption by a user according to one or more of the following steps. Providing a cartridge that includes a primary reservoir 508 containing an aerosol precursor composition, a mask 524, and a flavor reservoir 522 comprising a plurality of flavor sections 560. The method may also include adjusting the mask 524 relative to the flavor reservoir 522 to select one or more flavor sections 560. In some implementations, adjusting the mask may comprise aligning an outlet 578 in the mask 524 with an inner passage 566 of a selected flavor section 560 of the flavor reservoir 522. The method may further comprise directing a flow of air F through the selected flavor section 560 and to an atomizer chamber 540. Entraining flavorant into the flow of air F as the draw passes through the inner passage 566. The method further comprises adding particles of the aerosol precursor composition from the primary reservoir 508 that have been vaporized by an atomizer 510 to the flow of air F. Vaporizing the aerosol precursor composition may include directing an electrical current from a control body 200 to the atomizer 510 to aerosolize the aerosol precursor composition. In various implementations, aerosolizing the aerosol precursor composition may comprise heating a heater coil 514 that heats a liquid transport element 512 that contains the aerosol precursor composition so as to vaporize the aerosol precursor composition.

Figure 7:
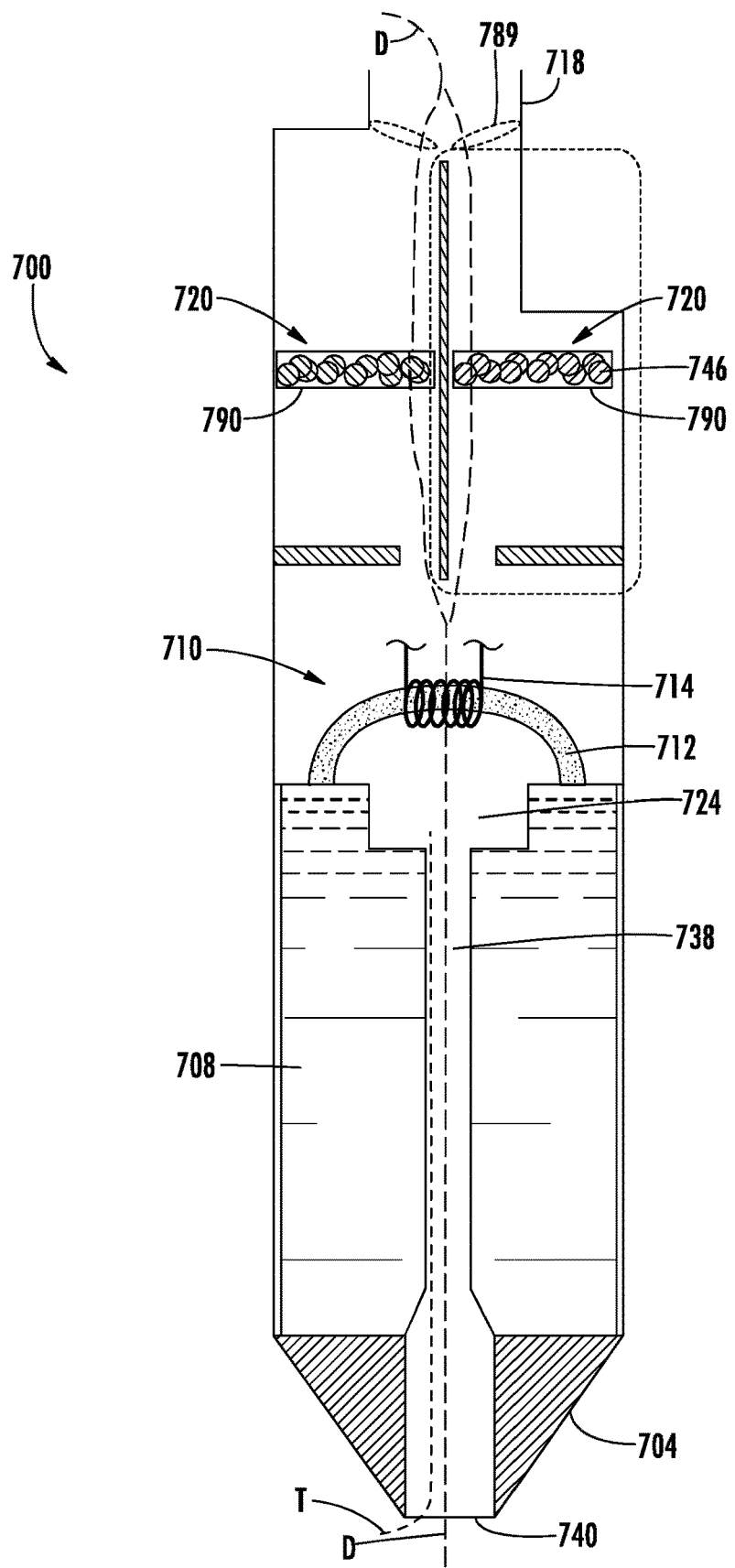
FIG. 7 illustrates a schematic cross section of a cartridge for use in an aerosol delivery device according to another example implementation of the present disclosure.
Figure 8:
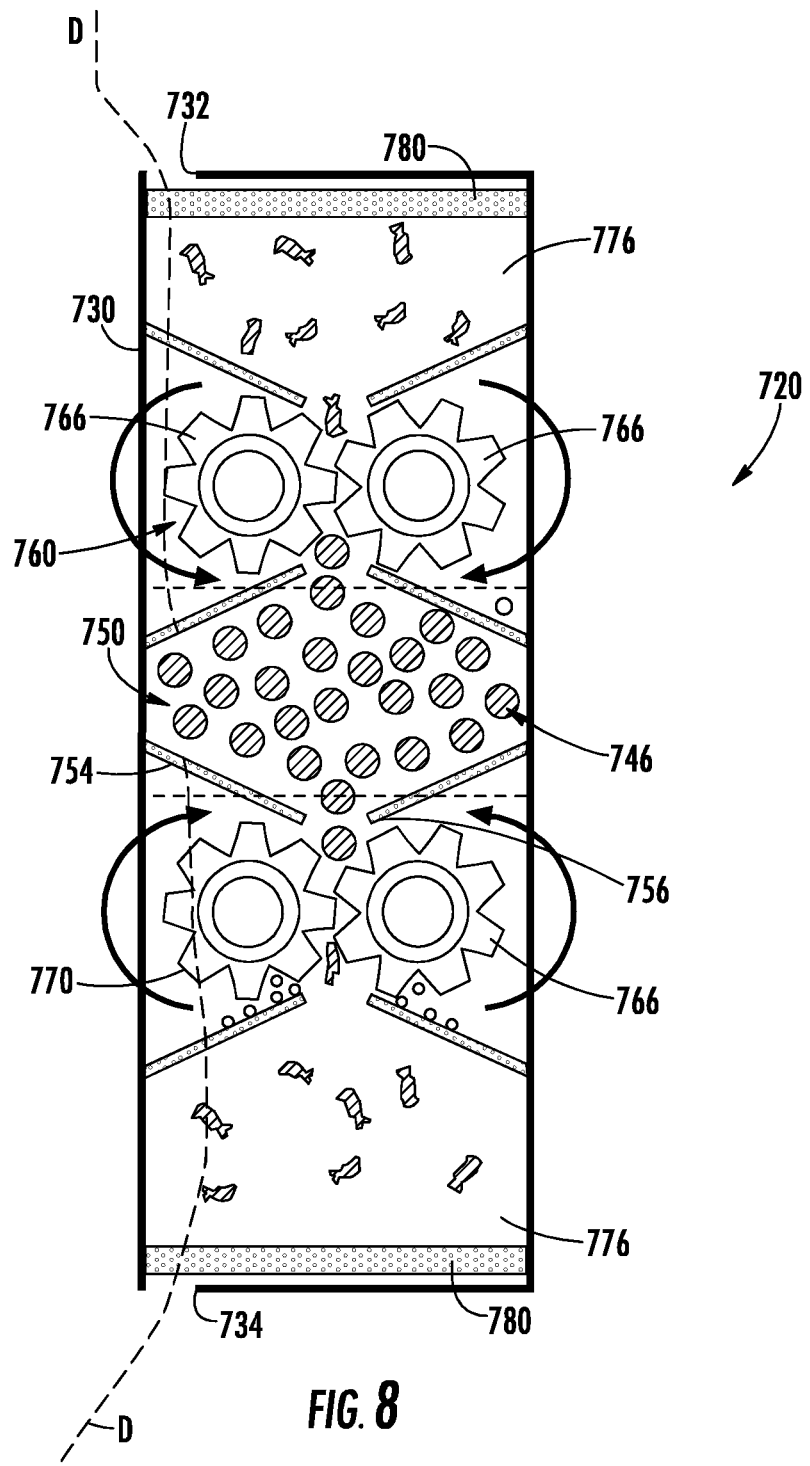
FIG. 8 illustrates a schematic cross section of a flavor adding module according to an example implementation of the cartridge of FIG. 7.

Turning now to another cartridge embodiment, FIG. 7 illustrates a schematic cross sectional view of a cartridge 700 for use in an aerosol delivery device, according to a second example implementation of the present disclosure. As illustrated in FIGS. 7-9, and as will be discussed in more detail below, the cartridge 700 of the depicted implementation includes the following components: a mouthpiece 704, a primary reservoir 708, an atomizer 710 (which includes a liquid transport element 712 and a heating element 714), a cartridge base 718, and one or more flavor adding modules 720. The flavor adding modules 720 may be considered as providing similar functionality as the flavor sections 560 of the cartridge 500 (FIG. 4), where a plurality of flavor adding modules 720 may combine to form a flavor reservoir that selectively incorporates flavorant into an aerosol drawn from the mouthpiece 704. The illustrated embodiment of FIG. 7 shows two flavor adding modules 720, but it should be understood that additional modules may be possible.

As understood from the discussion above, the cartridge 700 of FIGS. 7-9 may be configured to releasably engage a control body 200 (FIG. 2) with the cartridge base 718 so as to create an aerosol delivery device. In various implementations, the control body may be similar to, or the same as the control body 200 described above (see, FIG. 2), and hence description thereof will not be repeated. It should be noted, however, that in other implementations the control body may differ from that described above. In addition, in some implementations, the control body of the aerosol delivery device may have a different shape than that described above, such as, for example, a hand-held fob-shaped control body.

In principal, the cartridge 700 follows the same fundamentals of operation as the cartridge 500 (FIG. 4). Particularly, an aerosol precursor composition staged in the primary reservoir 708 is wicked by the liquid transport element 712 to the vicinity of the heating element 714. Upon activation of the heating element, particles of the aerosol precursor are vaporized into an atomizer chamber 724 where the particles are mixed with air drawn into the cartridge 700 and the atomizer chamber 724. Further, like the cartridge 500, the air D drawn through the cartridge 700 is also intended to selectively entrain flavorant T from the flavor reservoir or flavor adding modules 720, particularly where the particles of the flavorant have not been subject to heat induced vaporization from the atomizer 710. The flavor adding modules 720 may be positioned upstream of the atomizer chamber 724 as shown in FIG. 7 to receive an air flow prior to entraining aerosol precursor. Alternatively, the flavor adding modules 720 may be located downstream of the atomizer chamber to encounter an air flow that already includes particles of aerosol precursor. FIG. 8 illustrates a detailed schematic view of a flavor adding module 720 according to an implementation of the present embodiment. The flavor adding module 720 may include a housing 730 with an air inlet 732 and an air outlet 734, providing a chamber through which a flow of air may pass. In other embodiments, the flow of air may pass adjacent to instead of through the selected flavor adding module 720 where the flavor from the flavor adding module is released therefrom. In the illustrated embodiment, the air outlet 734 may lead to the atomizer chamber 724. In another embodiment, not shown, the air inlet 732 may be configured to be in communication with an aerosol channel 738 that passes from the atomizer chamber 724 and through the primary reservoir 708 to terminate at the air inlet 732. Then, the air outlet 734 may be in communication with an opening 740 in the mouthpiece 704, through which the consumer receives aerosol that includes the air D, particles of the aerosol precursor composition, and optionally particles of flavorant T.

The flavor adding module 720 provides the function of a flavor reservoir by staging flavorant that can be selectively added to the flow of air D through the cartridge 700. The illustrated implementation of the flavor adding module 720 may be highly suitable for use with flavorant provided in an encapsulated form, for example flavorant that is microencapsulated within a rupturable shell.

A representative microcapsule embodiment has an outer cover, shell, or coating that envelopes a liquid or solid core region, and in certain embodiments, the microcapsule can have a generally spherical shape. The core region, or "payload," such as the flavorant, is typically released when the outer shell undergoes some type of physical destruction, breakage, or other loss of physical integrity (e.g., through dispersion, softening, crushing, application of pressure, or the like).

Exemplary manners and methods for providing encapsulated materials, such as microencapsulated flavoring agents, are set forth in Gutcho, Microcapsules and Microencapsulation Techniques (1976) and Gutcho, Microcapsules and Other Capsules Advances Since 1975 (1979). Exemplary types of microcapsules can have diameters of less than 100 microns, and often can have outer shells that are gelatin based, cyclodextrin based, or the like. Microcapsules have been commercially available, and exemplary types of microcapsule technologies are of that type set forth in Kondo, Microcapsule Processing and Technology (1979); Iwamoto et al., AAPS Pharm. Sci. Tech. 2002 3(3): article 25; and U.S. Pat. No. 3,550,598 to McGlumphy and U.S. Pat. No. 6,117,455 to Takada et al.

Suitable larger capsules are commercially available from Mane Aromatic Flavors, located in Nice, France as gelatin encapsulated mixtures of medium chain triglycerides and flavor agents.

The outer shell of the capsule may be constructed of polymer or a food grade gelatin derived from bovine, piscine, or porcine stock. A wide variety of gelatins may be used, and the selection of a gelatin for the capsule outer surface is considered a matter of design choice to those of ordinary skill in the art. See, Kirk-Othmer, Encyclopedia of Chemical Technology, (4th Ed.) 12, 406-416 (1994), which is incorporated herein by reference. The type of gelatin used for constructing the outer shell of the capsule provides that capsule with the capability of being exposed to triacetin (a common plasticizer used in cigarette filter manufacture) or 1,2 propylene glycol (a common tobacco casing component) for relatively long periods of time without experiencing undesirable interaction (e.g., dissolution of the gelatin therein). Because the gelatins used in some embodiments may dissolve in water over extended periods of time, it is desirable to employ virtually anhydrous payloads (or payloads possessing very low amounts of water) with capsules having gelatin outer coatings.

In one embodiment, the payload is a mixture of a flavorant and a diluting agent. A diluting agent may be a triglyceride, such as a medium chain triglyceride, and more particularly a food grade mixture of medium chain triglycerides. See, for example, Radzuan et al., Porim Bulletin, 39, 33-38 (1999). Example flavorant of the payload have been discussed above.

The amount of flavorant and diluting agent within the capsule may vary. In some instances, the diluting agent may be eliminated altogether, and the entire payload can be composed of flavorant. Alternatively, the payload can be almost entirely comprised of diluting agent, and only contain a very small amount of relatively potent flavorant. In one embodiment using a capsule of, for example, approximately 3.5 mm in diameter, the weight of the liquid payload (e.g., flavorant and diluting agent) may be in the range of about 15 mg to about 25 mg, and may be in the range of about 20 mg to about 22 mg. One example composition of the mixture of flavorant and diluting agent is in the range of about 5 percent to about 25 percent flavorant, and possibly in the range of about 10 to about 15 percent flavorant, by weight based on the total weight of the payload, with the balance being diluting agent.

As shown in the illustrated implementation, the capsules 746 of flavorant may be staged in a portion of the flavor adding module 720 that may be referred to as a hopper 750. The hopper 750 may be defined by baffles 754 that are angled to channel the movement of the capsules 746 toward one or more exits 756. The baffles 754 may be formed from a porous material, such as porous polyethylene, polyester fibers, or porous ceramics, whose pores are small enough to be suitable for retaining the capsules 746. The pores in the baffles 754 can also minimize restriction of air flow from the inlet 732 to the outlet 734.

Each flavor adding module 720 may include an actuator 760. Alternatively, a single actuator 760 may be in operable communication with more than one flavor adding module 720. The actuator 760 may be provided for selectively releasing flavorant from the hopper 750. In the illustrated embodiment, the actuator 760 releases capsules 746 from the hopper 750. The actuator 760 then releases flavorant by applying pressure to rupture the coating of the capsule 746. In one implementation, the actuator 760 comprises one or more pairs of gears 766. As the pair of gears 766 rotate in opposite directions, as illustrated by arrows in FIG. 8, one or more capsules 746 may be pulled into or fall into the region between the gears. The teeth 770 of the gears 766 may then work together to apply a crushing force to the capsule 746, releasing the payload thereof to be absorbed by the porous baffles 754.

The capsules 746 and the payload thereof may be designed to accommodate the intended strength of the flavor and duration of flavor being incorporated into the flow of air. For example, the flavor adding module may be configured such that releasing the payload of one capsule with a single use of the actuator 760 provides enough flavor for enhancing multiple draws on the aerosol delivery device, such as the number of draws associated with a conventional cigarette. In other implementations, the capsules 746 may be configured with the intent that the user will operate the actuator 760 to release a small amount of flavorant prior to or during a draw on the device. One skilled in the art will appreciate that the user may be able to increase the strength of the flavor incorporated into the aerosol by triggering the actuator 760 multiple times to release the payload of multiple capsules 746. Similarly, the design of the actuator 760 and capsules 746 may be configured such that each operation of the actuator releases the payload from the desired quantity of capsules.

The flavor adding module 720 may be further designed with one or more repositories 776 configured to receive and maintain the outer coating material of the capsules 746 after the flavorant has been released. The boundary of the repository 776 may be defined, at least in part, by porous walls 780. Like the baffles 754, the walls 780 may be designed with pores that are too small to allow passage of the coating material of the capsules. The pores of the walls 780 would, however, be large enough to allow passage of the flow of air, as well as the passage of particles of the flavorant that are intended to become entrained in the flow of air D passing through the flavor adding module 720. The porous walls 780 can also act as a secondary structure for absorbing an flavorant released by the capsules 746 that otherwise bypasses the baffles 754.

Turning to FIGS. 9A and 9B, one example implementation is illustrated for causing rotation of the gears 766. A mechanical button 782 may extend from the flavor adding module 720 (FIG. 8) to a position accessible by the user. The button 782 may be mechanically linked to at least one of the gears 766 such that depression of the button causes rotation of the gears. FIG. 9A shows an initial position of the system, and FIG. 9B shows a depressed position of the system. Driving one gear 766 of a pair of gears can cause the other gear of the pair to rotate in an opposite direction as a result of the engagement between their respective teeth 770. Where more than one pair of gears 766 is provided as part of the actuator 760, the pairs may be operationally linked by additional gears, a drive belt, or another known motion transmitting element or elements.

The button 782 can be mechanically linked to at least one gear 766 through a drive rod 784 configured to translate linear motion of the button 782 to rotational motion of the gear 766. The drive rod 784 may terminate in a plunger 786. A spring 788 may be provided to act on the plunger 786 and assist returning the button 782 to its initial position.

Returning to FIG. 7, in one embodiment, the air D may be configured to simultaneously pass through each of the flavor adding modules 720 where the flavor entrained by the air D primarily includes the flavorant that was most recently released by the actuator 760. This approach, however, could result in undesirable residual flavorant as the user switches between modules. In another embodiment, an air flow controller 789, may be used to direct the flow of air through or passed only the desired flavoring adding module 720. The air flow controller 789 may be provided in the form of a flap or gate that can be controlled by various actuation devices, such as a mechanical button. In other embodiments, the air flow controller 789 can take the form of a mask, such as a rotatable mask as discussed above with respect to FIGS. 4-6.

As shown in FIG. 7, a body of the flavor adding module 720 and the cartridge 700 may be formed at least partially from a transparent or translucent material, for example, at least in a region corresponding with the hopper 750 to provide a window 790 into the hopper such that the amount of capsules 746 remaining in the hopper can be determined.

The foregoing description of use of the device can be applied to the various implementations described herein through minor modifications, which can be apparent to the person of skill in the art in light of the further disclosure provided herein. The above description of use, however, is not intended to limit the use of the article but is provided to comply with all necessary requirements of disclosure of the present disclosure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A cartridge for use in an aerosol delivery device, comprising:
   an airflow path extending through the cartridge;
   a reservoir configured to contain an aerosol precursor composition;
   an atomizer configured to vaporize the aerosol precursor composition to form a vapor that is entrained in air passing through the airflow path; and
   a flavor adding assembly comprising a plurality of separate chambers surrounded by an outer shell, at least one of the plurality of separate chambers containing a flavorant that surrounds an inner passage through the at least one of the plurality of separate chambers, the inner passage being positionable in the airflow path, and the inner passage being defined by a porous tube that is effective to transport the flavorant toward the inner passage so that the flavorant is entrained in the air passing through the inner passage.

2. The cartridge of claim 1, further comprising at least one mask moveably configured with the flavor adding assembly to selectively and alternatively permit the air to pass through the inner passage of the at least one of the plurality of separate chambers.

3. The cartridge of claim 1, wherein visual markings are provided on the cartridge to designate the chambers of the second reservoir.

4. The cartridge of claim 1, further comprising a hopper for staging the flavorant.

5. The cartridge of claim 4, further comprising an actuator for selectively releasing flavorant from the hopper.

6. The cartridge of claim 5, wherein the flavorant is encapsulated into a plurality of capsules.

7. The cartridge of claim 6, wherein the actuator is configured to break at least one of the capsules to release the flavorant.

8. The cartridge of claim 7, wherein the actuator comprises a pair of gears,
   wherein teeth of the gears cooperate such that rotation of the gears is configured to release at least one capsule from the hopper and release the flavorant from the capsule,
   wherein the flavorant is then entrained by the flow of air.

9. The cartridge of claim 5, wherein the actuator is triggered by a mechanical button.

10. The cartridge of claim 4, comprising a window into the hopper such that an amount of flavorant remaining in the hopper can be determined.

11. An aerosol delivery device, comprising:
    a control body; and
    a cartridge according to claim 1.

12. The aerosol delivery device of claim 11, wherein visual markings are provided on at least one of the cartridge and the control body to designate the chambers of the second reservoir.

13. The aerosol delivery device of claim 11, further comprising a hopper for staging the flavorant.

14. The aerosol delivery device of claim 13, further comprising an actuator for selectively releasing flavorant from the hopper.

15. The aerosol delivery device of claim 14, wherein the flavorant is encapsulated into a plurality of capsules.

16. The aerosol delivery device of claim 15, wherein the actuator is configured to break at least one of the capsules to release the flavorant.

17. The aerosol delivery device of claim 16, wherein the actuator comprises a pair of gears,
    wherein teeth of the gears cooperate such that rotation of the gears is configured to release at least one capsule from the hopper and release the flavorant from the capsule,
    wherein the flavorant is then entrained by the flow of air.

18. The aerosol delivery device of claim 14, wherein the actuator is triggered by a mechanical button.

19. The aerosol delivery device of claim 13, wherein the cartridge has a window into the hopper such that an amount of flavorant remaining in the chamber can be determined.

20. The cartridge of claim 1, wherein the flavor adding assembly comprises at least three chambers containing a flavorant and at least one chamber that does not contain a flavorant.

21. The cartridge of claim 1, wherein the porous tube is nanoporous or microporous.

22. The cartridge of claim 1, wherein the porous tube transports the flavorant through capillary action.

23. The cartridge of claim 2, wherein the mask is effective to permit air to flow through only one of the plurality of separate chambers at a time.

\* \* \* \* \*